United States Patent

Rzasa et al.

[11] 4,377,168
[45] Mar. 22, 1983

[54] CRYOSURGICAL INSTRUMENT

[75] Inventors: Ronald P. Rzasa, Fairfield; Ronald M. Wallach, Westport, both of Conn.

[73] Assignee: Wallach Surgical Instruments, Inc., Fairfield, Conn.

[21] Appl. No.: 236,521

[22] Filed: Feb. 27, 1981

[51] Int. Cl.³ ............................................. A61B 17/36
[52] U.S. Cl. .................................. 128/303.1; 128/399
[58] Field of Search ............................. 128/303.1, 399

[56] References Cited

U.S. PATENT DOCUMENTS

| Re. 28,657 | 12/1975 | Barger et al. |
| 3,393,679 | 7/1968 | Crump et al. |
| 3,451,395 | 6/1969 | Thyberg |
| 3,502,081 | 3/1970 | Amoils |
| 3,512,531 | 5/1970 | Crump et al. |
| 3,536,075 | 10/1970 | Thomas, Jr. |
| 3,548,829 | 12/1970 | Reynolds et al. |
| 3,613,689 | 10/1971 | Crump et al. |
| 3,696,813 | 10/1972 | Wallach |
| 3,782,386 | 1/1974 | Barger et al. |
| 3,901,241 | 8/1975 | Allen, Jr. |
| 3,913,581 | 10/1975 | Ritson et al. |
| 3,933,156 | 1/1976 | Riggi |
| 3,993,075 | 11/1976 | Lisenbee et al. |
| 4,015,606 | 4/1977 | Mitchiner et al. |
| 4,018,227 | 4/1977 | Wallach |
| 4,063,560 | 12/1977 | Thomas et al. |
| 4,146,030 | 3/1979 | Holroyd |

Primary Examiner—Kyle L. Howell
Assistant Examiner—Max F. Hindenburg

[57] ABSTRACT

A cryosurgical instrument having a cooling mode and a rapid warming or defrost mode is provided with a first conduit through which refrigerant gas is metered to undergo a Joule-Thomson or isoenthalpic expansion adjacent the tip of the instrument to cool the tip. The tip is defrosted by admitting a larger volume of unexpanded gas from the source to the tip through a second conduit and back pressurizing the gas to provide a sufficient balance to cause it to undergo heat exchange with the tip. Valve means, upstream from the tip is used to selectively control the gas flow path through either the first or second conduit. The tip is in communication with an exhaust port constantly open to the atmosphere. A pulse valve sensitive to gas volume in the exhaust line is positioned downstream from the tip between the tip and exhaust port to aid in back pressurizing the unexpanded gas by partially blocking the exhaust line. The pulse valve, however, bleeds the gas to the atmosphere to purge the gas from the instrument so the instrument can be rapidly switched to its cooling mode.

10 Claims, 14 Drawing Figures

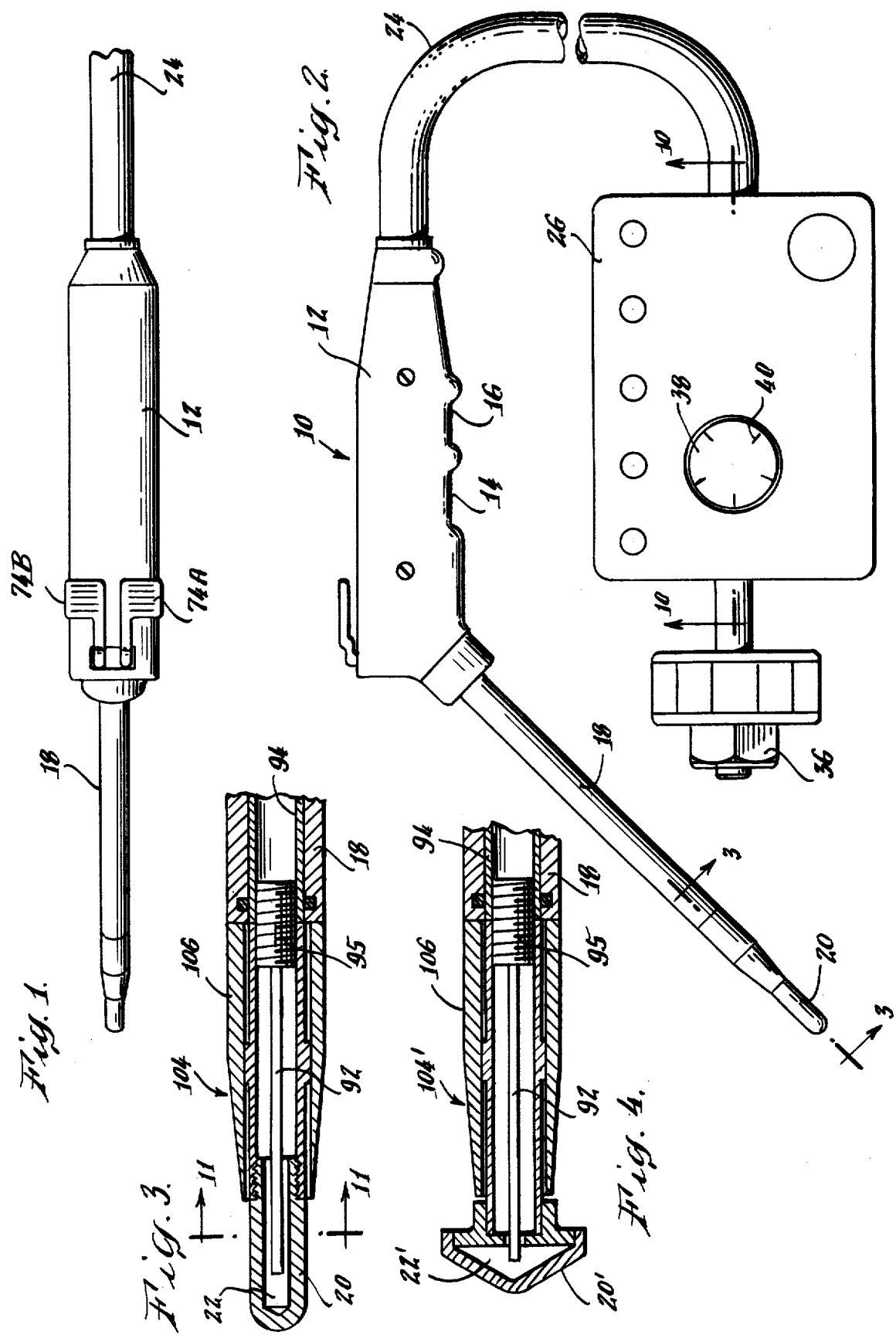

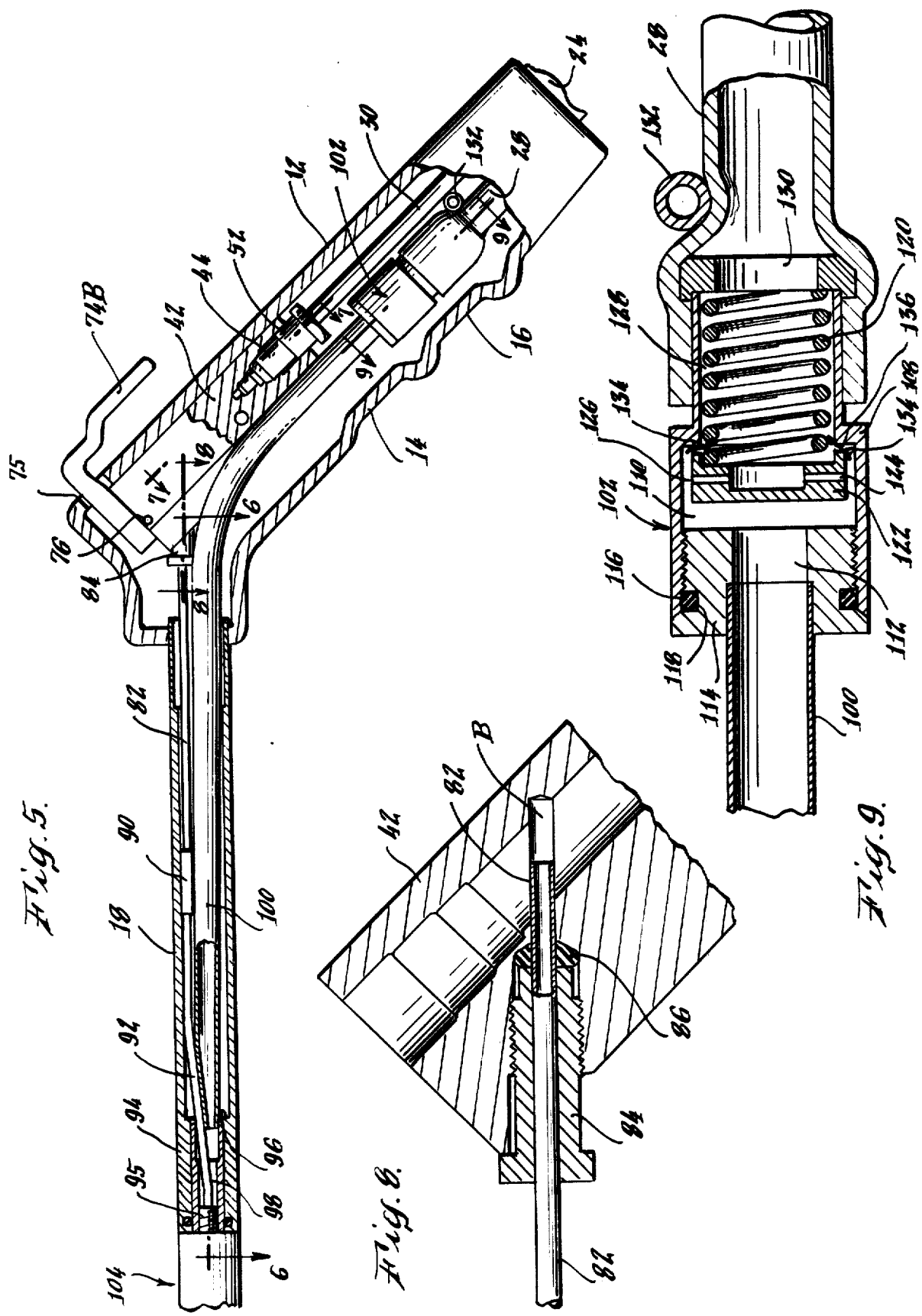

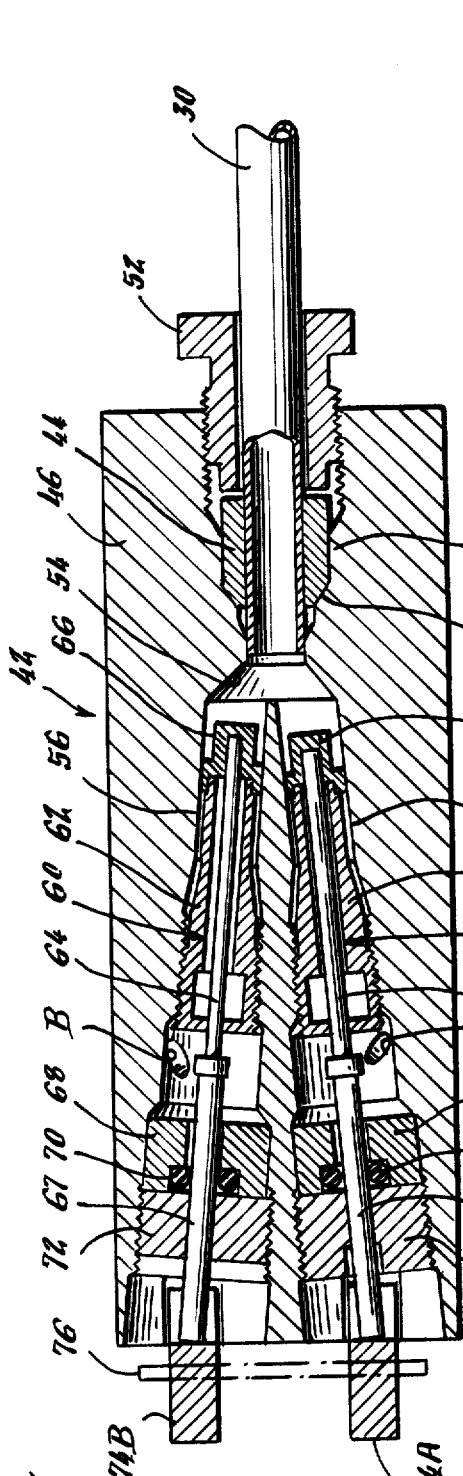

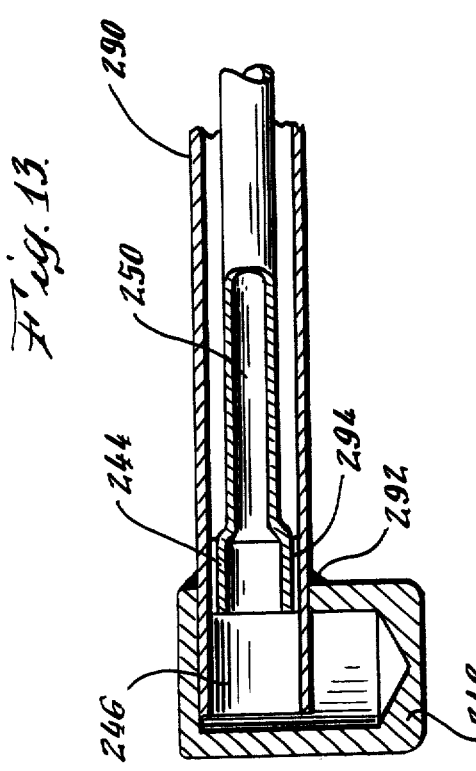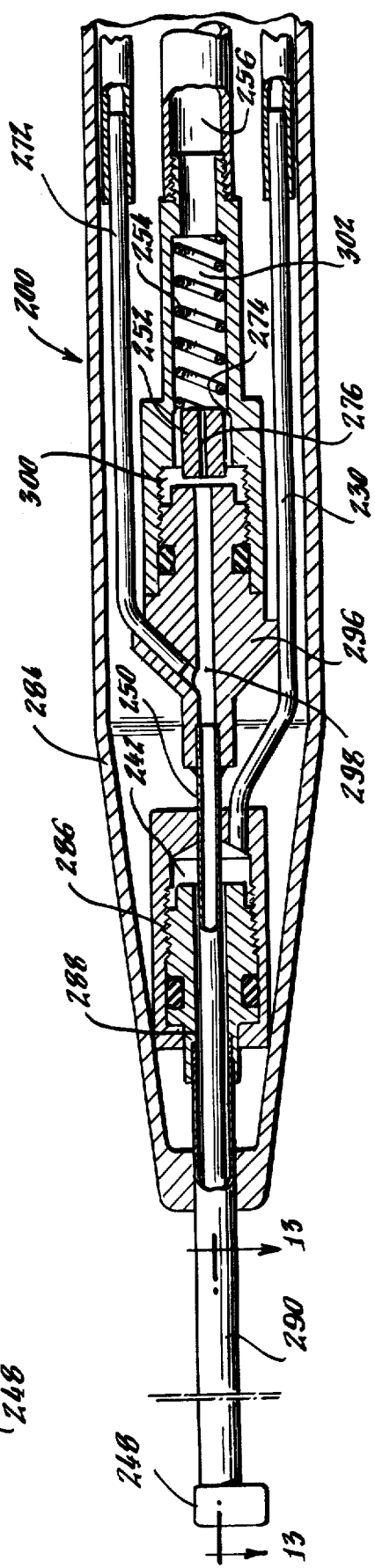

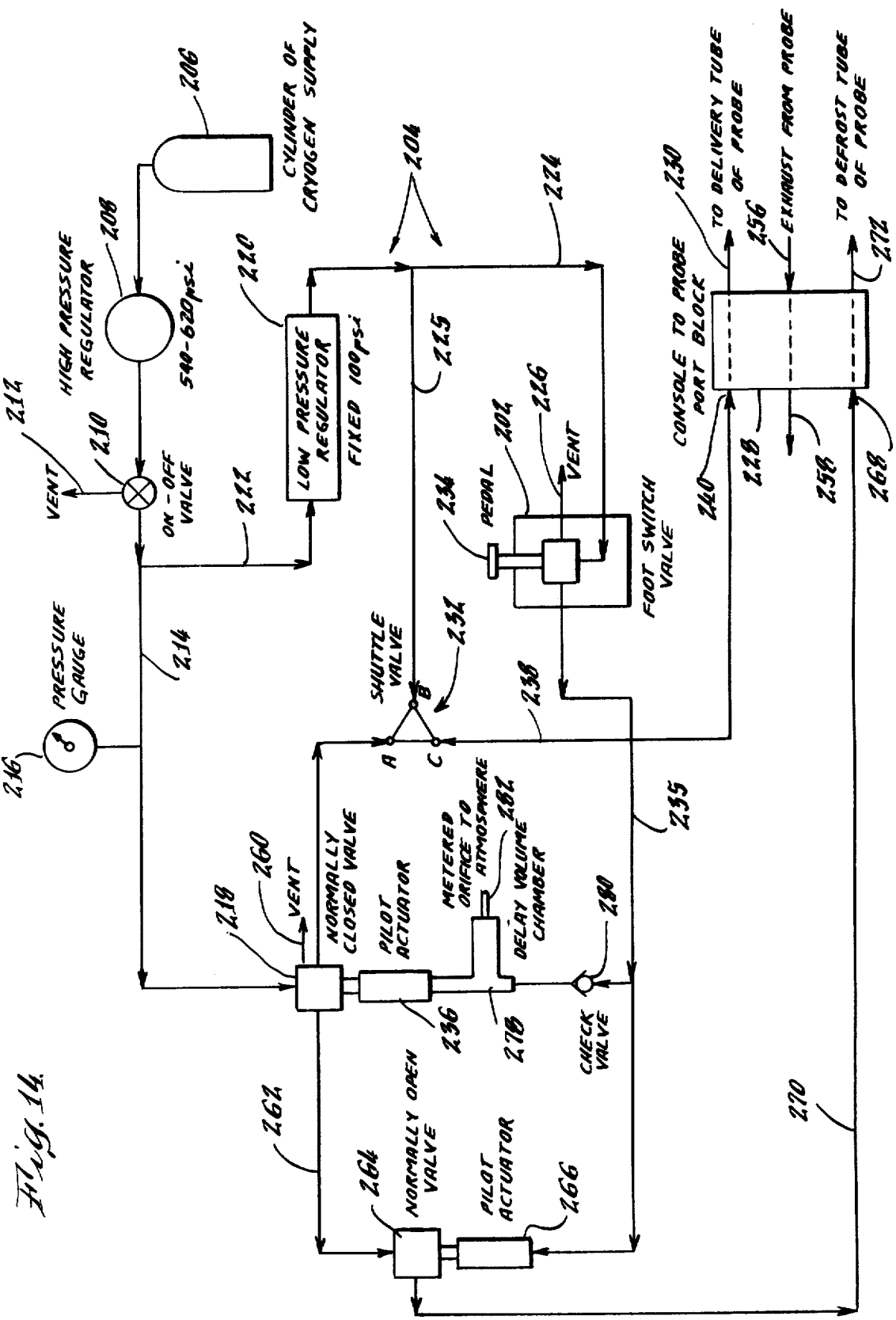

CRYOSURGICAL INSTRUMENT

TECHNICAL FIELD

This invention relates to cryosurgical instruments in which a hollow probe tip is cooled by the passage of a fluid refrigerant through the hollow interior of the tip.

In particular, the invention is concerned with instruments cooled by the Joule-Thomson effect or isenthalpic expansion of a gaseous refrigerant through a flow restriction adjacent the hollow interior or cavity of the tip. In the Joule-Thomson system, cooling is the result of the refrigerant fluid suffering a drop of pressure caused by the flow restriction through which the fluid passes. The restriction and consequently the cooling takes place within the instrument itself, and therefore the refrigerant reaches the tip of the instrument from the source at, or substantially at, the source pressure and temperature and the cooling occurs in the immediate vicinity of the tip. The refrigerant occupies the tip cavity of the instrument as a cold gaseous fluid cooled by isenthalpic gaseous expansion and takes up its latent heat of vaporization from the wall of the tip cavity and therefore from the tissue with which the probe is contacted. The cold gaseous fluid may carry with it some proportion of liquid refrigerant in the form of droplets or mist.

It is usually important that such a cryosurgical instrument be quickly and precisely controlled in the cooling, refrigeration, or "freezing" phase; while it is of comparable importance to control warming, defrosting, (or "thawing") of the instrument, particularly because it is desirable that it can quickly be released from the congelation with the tissue which it effects. Such warming involves a release or supply of heat, such as to raise the temperature of the probe and thereby the tissue and whatever other material constitutes their interface, such as saline solution deliberately used at such interface.

PRIOR ART

In the art of cryosurgical instruments, there have been proposed ways of warming the probe (to effect the warming mode) after using it as a refrigerated implement (i.e., in the freezing mode). In U.S. Pat. No. 3,502,081, Amoils disclosed in some detail electric resistance warming after a Joule-Thomson expansion to effect cooling. This technique is also disclosed by Allen in U.S. Pat. No. 3,901,241 in conjunction with evaporative cooling of a liquid refrigerant. This is cumbersome and expensive involving additional elements external to the probe.

In another type of cryosurgical instrument, e.g., disclosed in detail in U.S. Pat. No. 3,548,829 to Reynolds et al, U.S. Pat. No. 3,451,395 to Thyberg, and U.S. Pat. Nos. 3,393,679; 3,512,531 and 3,613,689 to Crump et al, the cooling of the hollow working tip of the instrument is provided by unseating a flow valve element in the return line located downstream from the tip and simultaneously forming a restrictive orifice at the inlet to the tip by contacting an orifice seat with a moveable conduit. Refrigerant liquid or gas then flows from a source through the orifice and exhausts through the unseated downstream valve to effect cooling of the tip by evaporation or by a Joule-Thomson expansion. Warming of the tip is accomplished by seating the downstream valve element and simultaneously separating the moveable conduit from the orifice seat, thus permitting refrigerant at ambient temperature to flood the hollow working tip. This instrument type requires a moveable conduit and valving that are complex and therefore difficult and expensive to make on a consistently reliable basis.

In U.S. Pat. Nos. 3,696,813 and 4,018,227, Wallach suggested warming by blocking the exhaust flow from the probe by closing a valve. Gas from the source, being rapidly increased in pressure would condense in the probe by reason of giving up latent heat, warming the probe. Wallach specifically proposed a cryosurgical instrument cooled by the Joule-Thomson effect, and warmed by blocking off the exhaust so that there would be a quick rise of pressure within the probe. The pressure of the supplied gas builds up within the probe until it balances the source pressure, the rate of flow of the gas entering the tip cavity of the probe by its ordinary path (i.e., through the refrigerating restriction) decreasing as the pressure difference between the pressure source and the cavity sink (i.e., the probe cavity and its immediately adjacent passage volumes) diminishes; likewise the rate of flow from the source to the sink, which is subject to the control exercised by the restriction, similarly decreases.

Designers of such instruments have to be alert to mechanical risk due to the fact that the whole structure of the probe (and any other elements similarly subjected to internal pressure) is subjected to the full source pressure when the instrument is in the warming mode. Since it is generally desirable to construct the probe tip with a very thin wall and it is in practice a necessity to provide various joints, there is some risk of mechanical failure. High thermal conductivity of the probe tip is desirable, and metals selected for high conductivity are often of low mechanical strength. Thus, from the purely mechanical point of view, the designer must have regard to the risk involved in the use of high internal pressure. Nevertheless, this risk is tolerable in some cases and is, in practice, to some extent mitigated by the simplicity of construction which it involves.

There is, however, also some disadvantage in exhaust blocking control from the fluidic or thermodynamic point of view. For example, in the warming mode when the exhaust valve is closed, refrigerant gas will liquify on some cooled surface in or connected with the instrument (e.g., tip cavity, exhaust passage, exhaust valve) at which fluid contact occurs; a considerable volume of liquid may thus accumulate. Should there be such an accumulation of liquid at a particular locality, negligible further heat is available for warming in the locality. This effect is likely to be greater in the instruments having larger mass, than in the smaller sizes, an example of which is an ophthalmic probe.

Another disadvantage of previously proposed exhaust blocking control is that in probes operating by the Joule-Thomson effect and in which the flow rate is limited by the refrigerating restriction to a very low rate, the rate of warming (being due to a similarly limited flow rate) will be correspondingly reduced.

Also, in such probes, leakage, e.g., past the exhaust valve, if of a similar order to passage through the refrigerating restriction, may result in failure to pressurize the cavity adequately and consequent inadequacy of warming.

U.S. Pat. No. 3,913,581 issued to Ritson and Thomas along with U.S. Pat. Nos. 3,782,386 and Re. 28,657 issued to Barger et al, U.S. Pat. No. 4,146,030 to Lisenbee all involve what is conveniently called "reverse flow" warming (as contrasted with "exhaust blocking" warming). Such constructions involve a provision in a Joule-Thomson type of instrument of a line of connection in which there is no deliberately provided restriction (but the volume, rate of flow of the gas is controlled or restricted in the freeze mode to undergo the Joule-Thomson expansion) between a source of pressurized gas and the cavity of a cryosurgical probe, so that the operator can operate valve means so as to admit warming gas at substantially ambient temperature at a high rate, into the cavity, usually through the unrestricted exhaust conduit or line (hence, the nomenclature "reverse-flow"), where such gas performs the required warming. The gas performs the warming largely or partially by condensing within the probe, the condensate then being allowed to escape as a liquid, or partly as a liquid and partly as a gas, being purged to atmosphere by following or entraining gas, the probe temperature having been raised by the latent heat. Liquid condensate remaining within the probe may be purged by venting or subsequently to warming, during the early part of the next cooling mode. While effective to provide a quick warming mode in small, e.g., ophthalmic instruments, in instruments adapted to operate on a larger scale, however, wherein by virtue of higher refrigerant flow through larger volumes, cooling of the exhaust passage (including exhaust valves) is greater, liquid condensate is likely to form preferentially in the exhaust rather than within the cavity, and may subsequently flow into the cavity, this leading to partial failure to warm or unacceptably slow warming. Finally, such instruments usually have hand- or foot-operated valves separate from the instrument itself. Consequently, they require separate consoles and extra high-pressure hose lines making the overall system more expensive, bulky and difficult to move about.

Also, in each of the aforementioned instruments, the valving to effect changing from the freeze to the defrost mode are provided on the exhaust side of the instrument. If the valving were located on the inlet side rather than the exhaust side, it would provide an unrestricted exhaust flow in the instrument resulting in better efficiency; a more maintenance-free instrument, since the valve would not encounter cryogenic temperatures; and a safer instrument since no high pressure gas condition would exist in the instrument in the static condition.

U.S. Pat. No. 3,536,075 is the only patent located which discloses such a construction; however, cooling is effected by evaporation of liquid refrigerant ducted to the tip, rather than a Joule-Thomson, isoentropic expansion of a refrigerant gas. This necessitates connecting the common exhaust line to a vacuum to remove the boiled gas and warm defrost liquid used to flood the tip, which would be inoperative in a Joule-Thomson instrument as insufficient back pressure of the gas would be generated, if the gas was sucked from the exhaust, to warm and defrost the tip after an isoentropic expansion of the gas.

U.S. Pat. Nos. 3,933,156 to Riggs and 4,015,606 are specific to constructions seeking to minimize some of the problems noted with respect to the prior art instruments.

For example, U.S. Pat. No. 3,933,156 to Riggs discloses insulating outer tubes surrounding concentric expansion tubes (i.e., an inlet and an exhaust tube) to minimize heat transfer between the tubes and condensation of refrigerant in the line of the process. In U.S. Pat. No. 4,015,606 Mitchiner discloses a cryosurgical instrument having a construction for controlling the freeze zone in the tip by moving the exhaust tube conduit in the tip towards or away from the supply (inlet) tube conduit.

SUMMARY OF THE INVENTION

The present invention relates to a cryosurgical instrument of the kind in which there is a probe having a tip or applicator with a wall of thermally conductive material enclosing a cavity. A supply of refrigerant fluid has its rate of flow controlled by passing it through a first duct having a flow restriction, expanding it with Joule-Thomson cooling in the tip, and permitting the resultant gas to escape through an exhaust duct.

In order to defrost the tip, a warming fluid is supplied into the cavity under pressure through a second duct while at substantially ambient temperature or at a temperature high relative to the probe temperature achieved in the cooling mode.

The cooling or freeze mode is activated by a trigger valve upstream from the probe tip. Trigger movement allows the flow of source cryogen gas, e.g., carbon dioxide or nitrous oxide, past a valve seat into a delivery tube or first duct which meters the volume of gas flowing through it so as to provide a correct pressure differential as it flows into the expansion cavity of the tip allowing an efficient Joule-Thomson or isoentropic expansion of the gas to occur. The spent gas flows out of the cavity into the annulus or space between the outside diameter of a defrost tube and the inside diameter of an exhaust tube. The spent or cold gas then flows into a pulse valve housing downstream from the tip. The pressure of the spent gas is insufficient to depress a spring that normally holds the pulse valve open, so the spent gas can flow around the pulse valve into an exhaust hose and out to atmosphere through an exhaust port.

To activate the warming or defrost mode, the freeze trigger is released and an adjacent defrost trigger upstream from the probe tip is depressed. Trigger movement allows the flow of the source cryogen gas past a valve seat into a defrost tube or second duct which meters the volume of gas to several magnitudes the volume that flows through the delivery tube or first duct. The warm, unexpanded gas flows into the expansion area in the tip and then into the exhaust tube and into the pulse valve housing. While in the tip, the warm gas condenses, giving up its latent heat to the surrounding tip to defrost the same. The pressure and volume of this gas is sufficient to depress the spring and close the pulse valve allowing the gas to flow only through drilled or bleed holes in the pulse valve. Although the gas flow through the bleed is of a higher magnitude than the gas flow during the freeze mode when the pulse valve is open, sufficient back pressure occurs because of the location and size of the bleed holes in the pulse valve so that defrost action takes place due to the warm defrost gas continuously flowing past the expansion chamber at sufficient back pressure, i.e., an unobstructed exhaust is provided to continuously purge a higher volume flow of warm gas in the defrost mode.

When the defrost trigger is released no new gas can enter the defrost tube and therefore the existing back pressure soon vents through the side bleed holes in the pulse valve dropping to a value less than that required to depress the spring. Therefore, the pulse valve piston returns to the open position, making the instrument ready for the freeze mode again, without purge or warm gas on the subsequent cycle, thereby providing for rapid defrost and cooling.

Because the valving to effect changing from the freeze to the defrost mode and vice-versa are located on the inlet side of the probe of the instrument, there is a continuous exhaust flow in both the freeze and defrost mode resulting in better efficiency as noted above, i.e., quicker freeze and defrost and the precluding of condensation in the exhaust tube; a more maintenance-free instrument since the trigger valves do not encounter cryogenic temperatures; and a safer instrument since no high pressure gas condition exists in the instrument in a static condition, the exhaust flow being continuous until depleted into the atmosphere.

BRIEF DESCRIPTION OF THE DRAWINGS

Further objects and advantages of the invention will become apparent from the following description and claims, and from the accompanying drawings, wherein:

FIG. 1 is a top plan view of the cryosurgical instrument of the present invention;

FIG. 2 is a side view in elevation of the cryosurgical instrument illustrated in FIG. 1;

FIG. 3 is a cross sectional view of the tip of the instrument illustrated in FIG. 2 taken substantially along the plane indicated by line 3—3;

FIG. 4 is a cross sectional view of an alternate form of tip which can be used with the cryosurgical instrument of FIGS. 1 and 2;

FIG. 5 is a longitudinal cross sectional view of the cryosurgical instrument illustrated in FIG. 2;

FIG. 6 is a cross sectional view taken substantially along the plane indicated by line 6—6 of FIG. 5;

FIG. 7 is a cross sectional view taken substantially along the plane indicated by line 7—7 of FIG. 5;

FIG. 8 is a cross sectional view taken substantially along the plane indicated by line 8—8 of FIG. 5;

FIG. 9 is a cross sectional view taken substantially along the plane indicated by line 9—9 of FIG. 5;

FIG. 10 is a cross sectional view taken substantially along the plane indicated by line 10—10 of FIG. 2;

FIG. 11 is a cross sectional view taken substantially along the plane indicated by line 11—11 of FIG. 3;

FIG. 12 is a longitudinal cross-sectional view of an alternate embodiment of a cryosurgical instrument of the present invention;

FIG. 13 is a cross-sectional view taken substantially along the plane indicated by line 13—13 of FIG. 12; and FIG. 14 is a schematic diagram of a valve console for use with the instrument of FIGS. 12 and 13.

DETAILED DESCRIPTION

Referring now to the drawings in detail, wherein like numerals indicate like elements throughout the several views, the cryosurgical instrument 10 of the present invention includes a steel or plastic outer housing 12 having a pair of indentations 14 and 16 into which the fingers of the user's hand can be placed to grip the housing 12. Extending outwardly from one end of the housing is a tube 18 having a hollow tip 20 threadedly connected at one end thereto and provided with a cavity 22. The tip 20 is made from a heat conductive metal and is adapted to contact tissue to be treated using the instrument 10. At its opposite end, the tube 18 is fixed by welding, brazing, swaging or the like, to the hollow housing 12.

At its opposite end, housing 12 is fixed to a flexible hose 24. Hose 24 extends outwardly from a port in a pressure gauge block 26. Housed within housing 12 is an exhaust tube 28 and a gas inlet tube 30. The exhaust tube 28 and inlet tube 30 are covered by flexible hose 24. Gas exhaust tube 28 is connected via a pressure gauge block 32 to an exhaust port 34 open to the atmosphere. Inlet tube 30 is also connected via the block 32 to a gas tank connector 36 to which a tank or bottle of nitrous oxide or carbon dioxide can be attached. Upon opening of the tank valve, gas will flow through connector 36, block 32 into the inlet line 30. A pressure gauge 38 has a tap into block 32 so that the pressure of the inlet gas can be readily ascertained on a dial face 40 on top of the gage 38.

Opening of the valve on the gas tank or cylinder admits gas into the pressure gauge assembly 26, registering the pressure on the gage dial 40 and admits gas into the inlet tube 30. The inlet tube is connected to an inlet valve assembly 42. Inlet valve assembly 42 includes a ferrule 44 slidably received in one end of a block 46. Ferrule 44 is received within a bore 48 having an annular shoulder 50. A nut 52 is threadedly received behind the ferrule 44 in bore 48. Nut 52 also receives the inlet tube 30 therethrough. Upon threading of nut 52 into bore 48, the forward end of the ferrule contacts annular shoulder 50 which causes the ferrule to clamp about the end of inlet tube 30 received therethrough.

Inlet tube 30 terminates in communication with an orifice 54. Orifice 54 has a first branch 56 and a second branch 58. Each branch includes an identical valve construction 60.

Valve construction 60 includes a hollow body member 62 threadedly received in each of the branch ports 56 and 58. A reciprocable plunger 64 extends through the hollow body member 62 and terminates in a cap 66 adapted to seat on one end of the hollow body member 62 and is movable towards and away from the same. The opposite end 67 of the plunger 64 extends through a continuation of branch port 56 and 58, through a seal 68 cooperating with an O-ring 70, a guide member 72 threadedly received in the upper end of each of the branch ports 56 and 58 and is in contact with a rotatable trigger 74A or 74B. The triggers 74A and 74B are each rotatably mounted on a pin 76 extending through the housing 12 in front of the valve block 46. Upon rotations of either of the triggers 74A or 74B, a rear surface of the trigger will contact the adjacent end 67 of plunger 64 and move it rearwardly through the corresponding branch port 56 or 58 unseating cap 66 from the hollow interior of its corresponding valve body 62, enabling gas to be conducted from orifice 54 into the interior of the valve body 62 and then through either a port A or a port B between the valve body 62 and the seal 68.

The cap 66 can be reseated upon the end of valve body 62 by a buildup of inlet gas behind the cap 66 and orifice 54 after release of the trigger 74A or 74B. Alternatively, a return spring can encircle the plunger 64 between an enlarged portion of its diameter and the cap 66 to effect a return force upon elongation of the spring upon depression of the trigger 74A or 74B.

In the freeze mode of the instrument, trigger 74A is depressed to admit gas through port A, while trigger 74B is depressed in the defrost mode to admit gas through port B.

As illustrated in FIGS. 6 and 8, ports A and B are in communication with the ends of a delivery conduit 80 and a defrost conduit 82, respectively. Each of the delivery and defrost conduits 80 and 82, respectively, extend through a tube retainer 84 threadedly received in spaced portions of inlet valve block 42. An O-ring seal 86 is placed between one end of the retainer 84 and the tube or conduit 80 or 82.

The delivery tube 80 has a reduced diameter portion 88 which extends through a union 90 into the interior of a coaxial defrost conduit 92 also joined to union 90 and in communication with the end of the defrost delivery tube 82. The defrost tube 92 with its coaxial inlet delivery tube 88 extends into an insulator sleeve 94. The insulator sleeve 94 is press fit within one end of the outer sheath 18 and has a shoulder 96 in abutment with an annular reduced diameter portion of the sheath 18. The interior bore 98 of insulator sleeve 94 which receives therethrough the coaxial defrost tube 92 and inlet delivery tube 88, is also in communication with the end of an exhaust conduit 100 which extends rearwardly along the sheath 18 and is press fitted at its rear end to an exhaust, pulse valve assembly generally indicated by the numeral 102.

Threadedly received on the forward end of insulator sleeve 94 is the tip assembly 104. The tip assembly 104 includes the thermoconductive tip 20 having a cavity 22, brazed to an outer insulator sleeve 106. Sleeve 106 has an internal portion threadedly received upon the threaded end 95 of insulator sleeve 94. The tip 20' illustrated in FIG. 4 is of substantially identical construction as that illustrated in FIG. 3, corresponding elements being indicated by corresponding numerals, except for the configuration thereof. The tip illustrated in FIG. 4 is used to necrose gynecological tissue while the tip illustrated in FIG. 3 is primarily for dermatology use to freeze small lesions. In either case, the coaxial defrost and inlet delivery tubes 88 and 92 are received through the sleeve 106 into the cavity 22 adjacent the outer wall of the tip 20 or 20'.

As illustrated in FIG. 9, the exhaust pulse valve assembly 102 includes a housing 108 having a bore 110 formed therethrough. Bore 110 includes a reduced diameter continuation portion 112 formed in a plug 114 threadedly received in one end of housing 108. An O-ring seal 116 is received in a groove 118 formed in plug 114 adjacent its threaded connection to the housing 102. Press fitted within reduced diameter bore 112 and in communication therewith and enlarged bore 110 of housing 108 in exhaust conduit 100.

The opposite end of housing 108 is press fitted and received within the end of exhaust tube 28, which is connected via the pressure gauge block 32 to the exhaust port 34.

Connected by coil spring 120 to housing 108 is floating pulse valve piston 122. The pulse valve piston 122 includes a pair of oppositely and diametrically opposed valve bleed ports 124 and 126 which provide communication between the interior of piston 122 and enlarged bore 110. The bore 110 is normally in communication with a second reduced diameter bore 128 within housing 108 within the interior coil spring 120, around the sides of piston 122. Bore 128 is in communication with an orifice 130 on the other end of housing 108, which in turn is in communication with the interior of exhaust tube 28. A bushing 132 separates the exhaust tube 28 from the inlet tube 30 within the interior of hollow housing 12.

In operation, a tank of cryogenic fluid such as nitrous oxide or carbon dioxide is connected to the gas cylinder attachment 36. Upon opening the valve on the cylinder tank of cryogen, gas is admitted under pressure through the pressure gauge assembly 26, registering the pressure on the gauge dial 40 and admitting gas to the inlet tube 30. The cryogenic gas is detained at the inlet side of the inlet valve assembly 42 in orifice 54.

In order to place the cryogenic instrument 10 in its freeze mode or condition, the trigger 74A is depressed, causing it to move to the rear of opening 75 and housing 12 about pin 76. Rotation of the trigger 74A about pin 76 causes it to contact end 67 of plunger 64 in branch conduit 58, causing it to move to the right or rear of the housing as viewed in FIGS. 5 and 7. This causes cap 66 on the end of plunger 64 to move to the right away from its seat with valve body 62 (first valve), admitting cryogenic gas from orifice 54 into the valve body 62, and through port A into the interior of the inlet delivery tube 80 and reduced diameter delivery tube 88 in coaxial relation with defrost tube 92. The gas egresses from the end of tube 88, which meters the volume of gas flowing through it so as to provide the correct pressure differential as it flows into tip cavity 22 allowing an efficient Joule-Thomson effect to occur or an isoentropic expansion, cooling the thermoconductive tip 20. The expanded or spent gas flows out of the cavity 22 into the interior of sleeve 106, through the bore in insulator sleeve 94 into the interior of exhaust tube 100. Spent or expanded gas then flows into the pulse valve housing 108. Pressure of this spent gas is insufficient to depress the piston 122 against the force of the coil spring 120 that holds valve piston 122 (second valve) in its floating or open condition within the enlarged bore 110, so that the spent gas flows around the pulse valve piston 122 as indicated by the arrows 134 through the bores 120 and 130, into the exhaust tube 28 and out the exhaust port 34.

In order to effect defrost of the cryosurgical instrument 10, the trigger 74B is depressed. The trigger 74B is likewise retained on pin 76 and rotates so that a rear portion thereof strikes the end 67 of plunger 64 which is moved towards the rear of valve block 42 moving the plunger 64 within the port branch 56 to the rear of the valve block 42 as illustrated in FIG. 7. This moves cap 66 away from the end of hollow valve body 62 in the branch port 56, and enables pressurized gas in orifice 54 to flow through the interior of valve body 62, through port B, defrost delivery tube 82, union 90, defrost conduit 92, and into the interior cavity 22 of tip 20 or interior cavity 22' of tip 20'. The larger defrost tube 92 meters the volume of gas to several times the magnitude of the volume that flows through the delivery tube 88 wherein the gas does not undergo a Joule-Thomson experiment, but remains warm and floods the cavity 22 of tip 22 or cavity 22' of tip 20'. The gas flows from the tip 22 into the exhaust conduit 100 into the enlarged bore 110 of the pulse valve housing 108. The pressure and volume of the unexpanded gas is sufficient to depress coil spring 120 and floating piston 122 to cause it to seat against an annular shoulder 136 in housing 108, allowing the gas to only flow through the bleed ports 124 and 126 into the interior bore 128, bore 130 and into the interior of the exhaust conduit 28 to be bled out the exhaust port 34. Although the gas flow through the bleed ports 124 and 126 is several times higher than the rate of gas flow during the freeze mode, sufficient back pressure occurs to retain warm gas within the tip cavity 22 or 22', which give up its latent heat of vaporization to the surrounding tip 20 or 20' to defrost the same. Therefore, defrost action takes place due to the high volume of warm defrost gas continuously flowing past the expansion chamber of cavity 22 in the tip 20 or cavity 22' in the tip 20', while creating sufficient back pressure.

This has several advantages as noted heretofore. Because of the continuous flow of gas through the instrument at the exhaust port, both during the freeze and defrost modes, no high pressure gas condition will ever exist in the instrument in the static condition, rendering it much safer than any instrument which has been proposed heretofore. Further, the exhaust side of the instrument never encounters cryogenic temperatures nor do the valves on the inlet side of the instrument, rendering the same more maintenance free. This is due to the trigger valves being provided on the inlet side, rather than the exhaust side of the expansion chamber or tip. Finally, by providing a continuous and unrestricted exhaust flow, better efficiency for the instrument is obtained since all the gases are scavenged or purged from the instrument before a new freeze cycle is initiated, precluding the gas from condensing anywhere but at the tip during the defrost cycle, thereby precluding condensation and blockage in the exhaust line.

When the defrost trigger 74B is released, no new gas can enter the defrost tube and therefore the existing back pressure soon vents through the bleed holes 124 and 126 in pulse valve floating piston 122 dropping to a value less than that required to depress coil spring 122 and seat the piston 122 on the seat or shoulder 136 of housing 108. Therefore, the pulse valve piston 122 returns to its normal floating, open position, enabling the cryogenic instrument 10 to immediately return to and enable the reinitiation of the freeze mode.

It should also be understood that in lieu of trigger elements 74A and 74B, any manual valve, such as a foot-operated valve, may be utilized.

For example, an ophthalmic-type cryosurgical probe 200, illustrated in FIGS. 12 and 13 may be connected to and operated by a foot-operated switch valve 202, through a console 204, schematically depicted in FIG. 14.

A suitable connector allows connecting the console 204 to a cylinder 206 of cryogen ($N_2O$ or $CO_2$). Opening master valve of the cylinder 206 allows the gas to enter a high pressure regulator 208 which can be adjusted from 540 psi to 620 psi, providing a consistent pressure for repeatable performance. The gas is conveyed to an on-off valve 210 from regulator 208. When the on-off valve is in the 'off' position all downstream gas is vented to atmosphere at 212. Turning the on-off valve 218 'on' allows gas to flow through two routes. The first route is to a low pressure regulator 220 through a line 222 that drops the pressure to 100 psi. This 100 psi gas flows through a line 224 to normally closed, manually operated 3-way footswitch valve 202, in which the downstream gas is vented to the atmosphere through port 226 in its normally closed position. The 100 psi gas also flows through line 225 to a console to probe port block 228 which connects the 100 psi gas to the delivery tube 230 of the probe 200. This 100 psi gas is used to purge moisture from the probe. This purge is constant and continuous. High pressure feedback to low pressure regulator 220 and footswitch valve 202 is restricted by a shuttle valve 232 in the line 225.

The pedal 234 of footswitch valve 202 is depressed to achieve the freeze mode. This allows 100 psi gas to flow through the footswitch valve 202 and line 235 to the pilot actuator 236 of the normally closed valve 218 allowing high pressure gas in line 214 to flow through the valve 218 and line 238 to the delivery tube 240 of the console to probe port block 228 allowing refrigerant to enter delivery chamber 242 of probe 200 past restrictor 244 expanding in the expansion area 246, thus cooling the tip 248. The spent gas flows through the inner tube 250 of the probe 200 around the pulse piston 252, which is held open by a spring 254 that exerts more pressure than that of the spent gas. This spent gas then flows out through an exhaust tube 256 back to the console to probe port block 228 and then to atmosphere through a vent 258. Being that normally closed valve 218 is vented in the closed position through port 260, shuttle valve 232 is used in the high pressure line 238 from the valve 218 to the console to probe port block 228 to prevent the purge flow from venting through the valve vent 260. High pressure gas also flows through line 262 from normally closed valve 218 to the inlet side of a normally open valve 264. This normally open valve is closed by its pilot actuator 266 receiving low pressure gas through line 235 in the freeze mode.

To defrost the probe 200, the footswitch pedal 234 is released. This causes the valve in the footswitch to close and immediately vent the gas that is actuating the pilot actuator 266 of the normally open valve 264 through vent 226. Therefore, normally open valve 264 opens and allows high pressure gas to flow through it from line 262 to the defrost tube port 268 of the console to probe port block 228 through line 270 and on to the defrost tube 272 of the probe 200. This gas entering the probe is of several magnitudes higher than the gas that is used for freezing. This defrost gas is sufficient in pressure and volume to depress the spring 254 holding the pulse piston 252 in the open position thus closing the pulse piston by causing it to seat against annular shoulder 274 allowing gas to flow only through a drilled passageway 276 through the center of pulse piston 252. Although the flow through the passageway 276 is higher than the flow around the pulse piston 252 when in the freeze mode, sufficient back pressure occurs causing high pressure gas to enter tube 250 and the hollow interior of tip 248, defrosting the tip. As this is occurring, gas is trapped in a delay volume chamber 278, received during the freeze mode and held therein by a check valve 280, being depleted through a metered orifice 282 venting chamber 278. Once depleted, the pilot actuator 236 of the normally closed valve 218 releases, thus closing the normally closed valve, shutting off the supply of high pressure gas to the normally closed valve 218 through port 260.

Since no new gas is entering the probe, all existing gas pressure vents quickly through the drilled passageway 276 of the pulse piston 252 and through the vent port 260 of the normally closed valve 218. When this residue pressure drops in value below the spring pressure exerted on the pulse piston 252, the pulse piston opens. The unit is now ready for the freeze mode again.

As shown in FIGS. 12 and 13, the delivery tube 230, defrost tube 272, pulse valve assembly, inner tube 250 and exhaust tube 256 may all be housed within a sheath or housing 284. Delivery tube 230 terminates in a block 286 housing delivery chamber 242 which is in communication with a bore 288 concentrically receiving inner tube 250 therethrough. Block 286 also has a tip support tube 290 connected to the forward end thereof in concentric relation to inlet tube 250. Tip support tube 290 is brazed or otherwise connected at 292 to tip 248. The forward end of tip support tube 290 provides the expansion area 246, while the forward end of inner tube 250 is flared at 244 to provide an annular, metered, Joule-Thomson restriction 294.

High pressure gas can thus flow in the freeze mode of the instrument through delivery tube 230 into delivery chamber 242, through bore 288 in block 286 in concentric relation to inner tube 250 and expand through annular restriction 294 into expansion area 246 to cool tip 248. The spent gas leaves through inner tube 250, which at its rear end is connected to pulse valve piston block 296 in communication with a bore 298 therethrough. Bore 298 terminates in a chamber 300 containing pulse valve piston 252. The spent gas enters chamber 300 from bore 298 in block 296, passes around piston 252 into spring bore 302 in communication with exhaust tube 256 connected to console to probe block 228 and vent 258 through which it is exhausted to the atmosphere.

In the defrost mode, high pressure gas enters defrost tube 272 from line 270 in the console to probe block 228. Defrost tube 272 is connected to pulse valve piston block 296 and is in communication with the interior of inner tube 250 and bore 298. The gas in bore 298 impinges upon pulse valve piston 252 to cause the same to seat against shoulder 274 and at the same time enters tip 248 through inner tube 250 to defrost the tip. The gas will bleed through passageway 276 in piston 252 and is discharged to atmosphere through chamber 302, exhaust tube 256, probe to console block 228 and vent 258, until depleted and the probe 200 is ready for freezing again.

Prior to initiation of the next freeze cycle, any residual moisture in the probe can be purged by admitting low pressure or 100 psi gas from the low pressure regulator 220 through line 225 and shuttle valve 232, line 238, port 240 and the console to probe block 228 to delivery tube 230. The low pressure gas will follow the path described above in connection with the freeze mode of the instrument and exhaust to atmosphere. However, the low pressure gas will not undergo a Joule-Thomson expansion as it passes through annular flow restriction 294, purging any moisture in the delivery and exhaust path.

We claim:

1. A cryosurgical instrument for use with a remote source of pressurized gas and adapted to operate in a cooling mode and in a rapid warming or defrost mode, comprising:
    a body having a wall of high thermal conductivity defining an enclosed cavity, said wall being shaped externally for contacting human tissue and providing heat transfer with the tissue and being of sufficient structural integrity to withstand the full force of a pressurized gas;
    a first conduit extending through said body and terminating adjacent said cavity for metering a pressurized gas therethrough so that said gas may expand into said cavity and undergo an isoenthalpic or Joule-Thomson expansion and in so doing cool said wall;
    a second conduit terminating in said cavity;
    an exhaust passage leading from said cavity to atmosphere; and
    first valve means for providing a cooling mode gas flow path from a source of pressurized gas, through said first conduit into said cavity and then through said exhaust passage, whereby the expansion of gas through said first conduit cools said wall, and for selectively providing a rapid warming or defrost mode gas flow path from said source of pressurized gas through said second conduit directly to said cavity for pressurizing said cavity sufficiently to condense said gas on the cool wall and liberate latent heat to warm the wall, and
    continuously open second valve means between said cavity and exhaust passage for selectively back pressuring said cavity during said cooling and rapid warming or defrost mode so that during said cooling mode there is insufficient back pressure on said gas continuously flowing through said cavity to cause the same to condense therein while during said rapid warming or defrost mode, there is sufficient back pressure on said gas to cause the same to condense and give up its latent heat of vaporization to said body enclosing said cavity to warm said body while allowing said gas to be continuously discharged from said instrument prior to reinstitution of said cooling mode.

2. A cryosurgical instrument in accordance with claim 1 wherein said second valve means includes
    a pulse valve having
    a floating piston adapted to close said exhaust passage in response to activation of said first valve means to provide said rapid warming or defrost mode gas flow path, and
    at least one bleed passage in said floating piston for directing gas to the atmosphere.

3. A cryosurgical instrument in accordance with claim 1 wherein said first valve means includes
    a first and second trigger-actuated valve mechanism for selectively providing said cooling mode and rapid warming mode gas flow paths, each of said valve mechanisms including
    a rotatable trigger element,
    a valve body having a gas conduit therein and a port in communication with said gas conduit and one of said first and second conduits,
    reciprocable plunger means extending through said valve body having an end in the path of rotation of said trigger element and an opposite end mounting a valve cap normally closing said conduit to preclude communication of said gas conduit therein with a source of pressurized gas,
    whereby rotation of its associate trigger element causes movement of said plunger means and unseating of said valve cap to enable pressurized gas to enter said valve body and flow through said port therein to the cavity in said body through one of said first and second conduits.

4. A cryosurgical instrument in accordance with claim 1 wherein at least a portion of said first and second conduits are coaxial.

5. A cryosurgical intrument in accordance with claim 1 including
    a third conduit terminating adjacent said cavity between said cavity and second valve means for forming said exhaust passage.

6. A cryosurgical instrument in accordance with claim 1 including
    a housing enclosing said first and second conduits, said exhaust passage and said second valve means, and
    said body being threadedly received on one end of said housing.

7. A cryosurgical instrument in accordance with claim 2 wherein said first valve means includes a first and second trigger-actuated valve mechanism for selectively providing said cooling mode and rapid warming mode gas flow paths, each of said valve mechanisms including a rotatable trigger element, a valve body having a gas conduit therein and a port in communication with said gas conduit and one of said first and second conduits, reciprocable plunger means extending through said valve body having an end in the path of rotation of said trigger element and an opposite end mounting a valve cap normally closing said conduit to preclude communication of said gas conduit therein with a source of pressurized gas, whereby rotation of its associate trigger element causes movement of said plunger means and unseating of said valve cap to enable pressurized gas to enter said valve body and flow through said port therein to the cavity in said body through one of said first and second conduits.

8. A cryosurgical instrument in accordance with claim 7 wherein at least a portion of said first and second conduits are coaxial.

9. A cryosurgical instrument in accordance with claim 8 including a third conduit terminating adjacent said cavity between said cavity and second valve means for forming said exhaust passage.

10. A cryosurgical instrument in accordance with claim 9 including a housing enclosing said first and second conduits, said exhaust passage and said first and second valve means, and said body being threadedly received on one end of said housing.

* * * * *